US006204368B1

(12) United States Patent
Heggie et al.

(10) Patent No.: US 6,204,368 B1
(45) Date of Patent: Mar. 20, 2001

(54) PROCESS FOR THE PURIFICATION OF ROXITHROMYCIN

(75) Inventors: William Heggie, Palmela; Alexandre Carvalho, Lisboa; Luis Sobral, Loures, all of (PT)

(73) Assignee: Hovione Inter Ltd. (PT)

( * ) Notice: Subject to any disclaimer, the term of this patent is extended or adjusted under 35 U.S.C. 154(b) by 0 days.

(21) Appl. No.: 09/372,522

(22) Filed: Aug. 11, 1999

(30) Foreign Application Priority Data

Sep. 10, 1998 (PT) ........................................ 102202

(51) Int. Cl.$^7$ ........................................ C07H 1/00
(52) U.S. Cl. .............................. 536/7.5; 536/7.2; 536/7.4; 536/127
(58) Field of Search ........................ 536/7.2, 7.4, 127, 536/7.5

(56) References Cited

U.S. PATENT DOCUMENTS 4,349,545  9/1982  Gouin d'Ambrieres et al. .... 536/7.2
5,959,088 * 9/1999  Miwa et al ............................ 536/72

FOREIGN PATENT DOCUMENTS

| 9400151   | 3/1997 | (AT) . |
| 0284203A2 | 9/1988 | (EP) . |
| 0284203A3 | 9/1988 | (EP) . |
| 2024371   | 2/1992 | (ES) . |
| 2026824   | 5/1992 | (ES) . |
| 2036472   | 5/1993 | (ES) . |

* cited by examiner

*Primary Examiner*—Elli Peselev
(74) *Attorney, Agent, or Firm*—Ostrolenk, Faber, Gerb & Soffen, LLP

(57) ABSTRACT

A process for the purification of roxithromycin, an antibiotic for therapeutic purposes, in which the purification is carried out by the dissolution or suspension of the product in methanol followed by cooling. Purification may also be obtained by addition of a non-solvent and/or by concentration of the mixture, thus obtaining a purified product.

6 Claims, No Drawings

PROCESS FOR THE PURIFICATION OF ROXITHROMYCIN

The present invention refers to a process for the purification of roxithromycin by crystallisation of methanol, possibly in the presence of water.

AT9400151 describes a process for the purification of roxithromycin by crystallisation with a halogenated solvent, namely chloroform. The usage of chloroform at an industrial level is not advisable as it is considered a hazardous solvent for the environment and, it is also not advisable to use it in the last step of the synthesis route since it is considered as potentially cancerous.

U.S. Pat. No. 4,349,545 describes a process for the purification of roxithromycin by crystallisation with acetone and water, where the product is dissolved in warm acetone and the crystallisation caused by addition of water. Mixtures of acetone and water are not efficient in the reduction of the impurity (impurity A) which appears immediately after the roxithromycin peak in the high-pressure liquid chromatography system of the European Pharmacopoeia. The reduction of this impurity is crucial since the European Pharmacopoeia establishes an individual limit of impurities at 0.5% and this impurity may have levels higher than 2% in the impure roxithromycin.

ES2026824 and ES2024371 describe processes of purification by column chromatography, which are expensive when applied to an industrial scale.

A simple process is described to purify the roxitromycin without the disadvantages mentioned above. The purification method consists of dissolving the impure roxithromycin in methanol and then start the crystallisation by cooling off or by addition of water. The present invention also takes advantage of roxithromycin solubility in methanol. Surprisingly, the roxithromycin solubility in methanol is low in comparison to other common alcohols, namely ethanol and isopropyl alcohol, or even to other common organic solvents such as acetone.

The crystallisation method consists of dissolving the impure roxithromycin at a temperature near to that of the reflux temperature of methanol and then slowly cooling until the mixture becomes turbid. Turbidity occurs at a temperature around 51° C. After turbidity it may be possible to seed the mixture with roxithromycin of good quality. The mixture is stirred for approximately 30 minutes, maintaining the range of the turbidity temperature. Thereafter, the mixture is cooled slowly, in a controlled fashion until approximately 0° C. Preferably the cooling off should follow the following cooling pattern, 3° C. in the first hour, 4° C. in the second hour, 6° C. between the third and the fifth hour and 9° C. in the remaining period. The solution is filtered and the purified solid washed with a mixture of methanol and water, previously cooled to approximately 0° C. The solid is dried at a temperature between 40° and 60° C.

The purification method herein described allows reducing in an efficient way the impurities present in the roxithromycin, especially the impurity A.

Optionally, the roxithromycin may also be dissolved at a temperature of approximately 40° C. and maintaining this temperature, water added slowly until the mixture is turbid. Thereafter, the mixture is stirred at approximately 40° C. for one hour and then cooled to approximately 0° C. The solution is filtered and the purified solid washed with a mixture of methanol and water previously cooled to approximately 0° C. The solid is dried at a temperature between 40° and 60° C.

It is also possible to purify the roxithromycin by suspension in methanol. In this case impure roxithromycin is suspended in methanol, and stirred for about 2 hours at a temperature of around 40° C. The suspension is cooled slowly to approximatley 0° C. with good stirring. Thereafter it is filtered and the purified solid is washed with methanol previously cooled to approximately 0° C. The solid is dried at a temperature between 40° and 60° C.

Another methanol purification method consists of dissolving, at room temperature, the impure roxithromycin in methanol and then, at this temperature, concentrate the solution under vacuum until having destined the adequate volume of solvent. The mixture is cooled off slowly to about 0° C. and stirred for 1 hour at this temperature. The solution is filtered and the solid is washed with methanol previously cooled to approximately 0° C. The solid is dried at a temperature between 40° and 60° C.

The following examples serve to illustrate the different aspects of the invention:

EXAMPLE 1

220 ml methanol were added to 100 g of roxithromycin with 96.1% purity by h.p.l.c. and 2.1% of the impurity A, heating until dissolution. The solution was slowly cooled until beginning of turbidity and was then seeded with good quality roxithromycin. Thereafter it was stirred for half an hour maintaining the temperature and then cooling with control until 0° C. The solid was filtered and washed with a mixture of methanol and water previously cooled to 0° C. After drying, 82 g of a product with 99.4% purity and 0.4% of the impurity A was obtained.

EXAMPLE 2

20 g of roxithromycin with 97.2% purity by h.p.l.c. and 1.5% of the impurity A were suspended in 60 ml methanol and stirred at 40° C. for two hours. The mixture was cooled to room temperature and stirred for one hour at 0° C. The solid was filtered and washed with methanol previously cooled to 0° C. After drying, 14.4 g of a product with 99.0% purity and 0.4% of the impurity A.

EXAMPLE 3

60 ml methanol were added to 10 g roxithromycin with 96.5% purity by h.p.l.c. and 2.2% of the impurity A, heating to 40° C. and maintaining this temperature, slowly adding water until turbidity. The mixture was stirred for one hour at this temperature and was then cooled to room temperature, stirring for one hour at 0°/5° C. The solid was filtered and washed with a mixture of methanol and water, previously cooled to 0° C. 7.9 g of a product with 99.4% purity and 0.4% of the impurity A.

EXAMPLE 4

130 ml methanol were added to 10 g roxithromycin with 97.7% purity by h.p.l.c. And 1.3% of the impurity A, and stirred until dissolution. The mixture was concentrated with vacuum at room temperature until 40 ml of solvent was distilled. At atmospheric pressure the mixture was cooled to 0° C. and stirred for one hour at this temperature. The solid was filtered and washed with methanol previously cooled to 0° C. After drying, 3.5 g of a product with 99.0% purity and 0.4% of the impurity A.

What is claimed is:

1. A process for the purification of roxithromycin, wherein the product is crystallised or suspended in methanol and the purified roxithromycin is recovered from the mixture.

2. A process according to claim 1, wherein the impure roxithromycin is dissolved, or partially dissolved and suspended in methanol with heating and the purified product is obtained by cooling the mixture.

3. A process according to claim 1, wherein the impure roxithromycin is dissolved, or partially dissolved and suspended in methanol and the purified product is obtained by addition of a non-solvent, optionally with heating.

4. A process according to claim 3, wherein the non-solvent is water.

5. A process according to claim 1, wherein the impure roxithromycin is dissolved, or partially dissolved and suspended in methanol and the purified product is obtained by concentration of the mixture.

6. A process according to claim 1, wherein the impure roxithromycin is dissolved, or partially dissolved and suspended in methanol with heating and the purified product is obtained by combination of two or more of the steps of (a) cooling the mixture, (b) addition of a non-solvent, optionally with heating and (c) concentration of the mixture.

* * * * *